US011730457B2

(12) United States Patent
Locke et al.

(10) Patent No.: US 11,730,457 B2
(45) Date of Patent: Aug. 22, 2023

(54) IN-LINE DIAGNOSTIC TOOL FOR NEGATIVE-PRESSURE THERAPY

(71) Applicant: KCI Licensing, Inc., San Antonio, TX (US)

(72) Inventors: Christopher Brian Locke, Bournemouth (GB); Justin Alexander Long, Bournemouth (GB); Timothy Mark Robinson, Shillingstone (GB)

(73) Assignee: KCI Licensing, Inc., San Antonio, TX (US)

( * ) Notice: Subject to any disclaimer, the term of this patent is extended or adjusted under 35 U.S.C. 154(b) by 528 days.

(21) Appl. No.: 16/325,124

(22) PCT Filed: Aug. 10, 2017

(86) PCT No.: PCT/US2017/046265
§ 371 (c)(1),
(2) Date: Feb. 12, 2019

(87) PCT Pub. No.: WO2018/034932
PCT Pub. Date: Feb. 22, 2018

(65) Prior Publication Data
US 2021/0290207 A1 Sep. 23, 2021

(51) Int. Cl.
*A61B 10/00* (2006.01)
*A61F 13/00* (2006.01)
*A61M 1/00* (2006.01)

(52) U.S. Cl.
CPC .... *A61B 10/0045* (2013.01); *A61F 13/00068* (2013.01); *A61M 1/95* (2021.05);
(Continued)

(58) Field of Classification Search
CPC ............... A61F 13/00068; A61M 1/90; A61M 2205/584; A61B 2010/0006
See application file for complete search history.

(56) References Cited

U.S. PATENT DOCUMENTS 1,355,846 A 10/1920 Rannells
2,547,758 A 4/1951 Keeling
(Continued)

FOREIGN PATENT DOCUMENTS

AU 550575 B2 3/1986
AU 745271 B2 3/2002
(Continued)

OTHER PUBLICATIONS

Louis C. Argenta, MD and Michael J. Morykwas, PHD; Vacuum-Assisted Closure: A New Method for Wound Control and Treatment: Clinical Experience; Annals of Plastic Surgery; vol. 38, No. 6, Jun. 1997; pp. 563-576.
(Continued)

*Primary Examiner* — Sarah Al Hashimi
*Assistant Examiner* — Nhu Q. Tran

(57) ABSTRACT

A sampling interface may comprise an inlet port, an outlet port, and a sampling chamber between the inlet port and the outlet port. The apparatus may also comprise a sampling port and at least one split seal between the sampling port and the sampling chamber. The split seal may comprise a first sealing member and a second sealing member that converge to a sealing line. The apparatus may additionally include at least one fluid collection channel disposed interior to the split seal. A lateral flow strip for sampling fluid removed from a tissue site may comprise an acquisition surface and a migration medium fluidly coupled to the acquisition surface. At least one test medium may be fluidly coupled to the migration medium, and a liquid-impermeable cover may enclose the migration medium and the test medium. The acquisition surface is preferably not enclosed.

10 Claims, 11 Drawing Sheets

(52) U.S. Cl.
CPC ........ *A61B 2010/0006* (2013.01); *A61M 1/92* (2021.05); *A61M 2205/584* (2013.01)

(56) References Cited

U.S. PATENT DOCUMENTS

| | | | |
|---|---|---|---|
| 2,632,443 A | 3/1953 | Lesher | |
| 2,682,873 A | 7/1954 | Evans et al. | |
| 2,910,763 A | 11/1959 | Lauterbach | |
| 2,969,057 A | 1/1961 | Simmons | |
| 3,066,672 A | 12/1962 | Crosby, Jr. et al. | |
| 3,367,332 A | 2/1968 | Groves | |
| 3,520,300 A | 7/1970 | Flower, Jr. | |
| 3,568,675 A | 3/1971 | Harvey | |
| 3,648,692 A | 3/1972 | Wheeler | |
| 3,682,180 A | 8/1972 | McFarlane | |
| 3,826,254 A | 7/1974 | Mellor | |
| 4,080,970 A | 3/1978 | Miller | |
| 4,096,853 A | 6/1978 | Weigand | |
| 4,139,004 A | 2/1979 | Gonzalez, Jr. | |
| 4,165,748 A | 8/1979 | Johnson | |
| 4,184,510 A | 1/1980 | Murry et al. | |
| 4,233,969 A | 11/1980 | Lock et al. | |
| 4,245,630 A | 1/1981 | Lloyd et al. | |
| 4,256,109 A | 3/1981 | Nichols | |
| 4,261,363 A | 4/1981 | Russo | |
| 4,275,721 A | 6/1981 | Olson | |
| 4,284,079 A | 8/1981 | Adair | |
| 4,297,995 A | 11/1981 | Golub | |
| 4,333,468 A | 6/1982 | Geist | |
| 4,373,519 A | 2/1983 | Errede et al. | |
| 4,382,441 A | 5/1983 | Svedman | |
| 4,392,853 A | 7/1983 | Muto | |
| 4,392,858 A | 7/1983 | George et al. | |
| 4,419,097 A | 12/1983 | Rowland | |
| 4,465,485 A | 8/1984 | Kashmer et al. | |
| 4,475,909 A | 10/1984 | Eisenberg | |
| 4,480,638 A | 11/1984 | Schmid | |
| 4,525,166 A | 6/1985 | Leclerc | |
| 4,525,374 A | 6/1985 | Vaillancourt | |
| 4,540,412 A | 9/1985 | Van Overloop | |
| 4,543,100 A | 9/1985 | Brodsky | |
| 4,548,202 A | 10/1985 | Duncan | |
| 4,551,139 A | 11/1985 | Plaas et al. | |
| 4,569,348 A | 2/1986 | Hasslinger | |
| 4,605,399 A | 8/1986 | Weston et al. | |
| 4,608,041 A | 8/1986 | Nielsen | |
| 4,640,688 A | 2/1987 | Hauser | |
| 4,655,754 A | 4/1987 | Richmond et al. | |
| 4,664,662 A | 5/1987 | Webster | |
| 4,710,165 A | 12/1987 | McNeil et al. | |
| 4,733,659 A | 3/1988 | Edenbaum et al. | |
| 4,743,232 A | 5/1988 | Kruger | |
| 4,758,220 A | 7/1988 | Sundblom et al. | |
| 4,787,888 A | 11/1988 | Fox | |
| 4,826,494 A | 5/1989 | Richmond et al. | |
| 4,838,883 A | 6/1989 | Matsuura | |
| 4,840,187 A | 6/1989 | Brazier | |
| 4,863,449 A | 9/1989 | Therriault et al. | |
| 4,872,450 A | 10/1989 | Austad | |
| 4,878,901 A | 11/1989 | Sachse | |
| 4,897,081 A | 1/1990 | Poirier et al. | |
| 4,906,233 A | 3/1990 | Moriuchi et al. | |
| 4,906,240 A | 3/1990 | Reed et al. | |
| 4,919,654 A | 4/1990 | Kalt | |
| 4,941,882 A | 7/1990 | Ward et al. | |
| 4,953,565 A | 9/1990 | Tachibana et al. | |
| 4,969,880 A | 11/1990 | Zamierowski | |
| 4,985,019 A | 1/1991 | Michelson | |
| 5,037,397 A | 8/1991 | Kalt et al. | |
| 5,086,170 A | 2/1992 | Luheshi et al. | |
| 5,092,858 A | 3/1992 | Benson et al. | |
| 5,100,396 A | 3/1992 | Zamierowski | |
| 5,134,994 A | 8/1992 | Say | |
| 5,149,331 A | 9/1992 | Ferdman et al. | |
| 5,167,613 A | 12/1992 | Karami et al. | |
| 5,176,663 A | 1/1993 | Svedman et al. | |
| 5,215,522 A | 6/1993 | Page et al. | |
| 5,232,453 A | 8/1993 | Plass et al. | |
| 5,261,893 A | 11/1993 | Zamierowski | |
| 5,278,100 A | 1/1994 | Doan et al. | |
| 5,279,550 A | 1/1994 | Habib et al. | |
| 5,298,015 A | 3/1994 | Komatsuzaki et al. | |
| 5,342,376 A | 8/1994 | Ruff | |
| 5,344,415 A | 9/1994 | DeBusk et al. | |
| 5,358,494 A | 10/1994 | Svedman | |
| 5,417,673 A * | 5/1995 | Gordon | A61M 39/045 604/86 |
| 5,437,622 A | 8/1995 | Carion | |
| 5,437,651 A | 8/1995 | Todd et al. | |
| 5,527,293 A | 6/1996 | Zamierowski | |
| 5,549,584 A | 8/1996 | Gross | |
| 5,556,375 A | 9/1996 | Ewall | |
| 5,607,388 A | 3/1997 | Ewall | |
| 5,636,643 A | 6/1997 | Argenta et al. | |
| 5,645,081 A | 7/1997 | Argenta et al. | |
| 6,053,861 A | 4/2000 | Grossi | |
| 6,071,267 A | 6/2000 | Zamierowski | |
| 6,135,116 A | 10/2000 | Vogel et al. | |
| 6,241,747 B1 | 6/2001 | Ruff | |
| 6,287,316 B1 | 9/2001 | Agarwal et al. | |
| 6,345,623 B1 | 2/2002 | Heaton et al. | |
| 6,364,847 B1 * | 4/2002 | Shulze | A61B 5/150236 600/580 |
| 6,488,643 B1 | 12/2002 | Tumey et al. | |
| 6,493,568 B1 | 12/2002 | Bell et al. | |
| 6,553,998 B2 | 4/2003 | Heaton et al. | |
| RE38,145 E | 6/2003 | Lynn | |
| 6,814,079 B2 | 11/2004 | Heaton et al. | |
| 6,908,459 B2 * | 6/2005 | Harding | A61M 39/26 604/533 |
| 7,004,915 B2 | 2/2006 | Boynton et al. | |
| 7,846,141 B2 | 12/2010 | Weston | |
| 8,062,273 B2 | 11/2011 | Weston | |
| 8,216,198 B2 | 7/2012 | Heagle et al. | |
| 8,251,979 B2 | 8/2012 | Malhi | |
| 8,257,327 B2 | 9/2012 | Blott et al. | |
| 8,398,614 B2 | 3/2013 | Blott et al. | |
| 8,449,509 B2 | 5/2013 | Weston | |
| 8,529,548 B2 | 9/2013 | Blott et al. | |
| 8,535,296 B2 | 9/2013 | Blott et al. | |
| 8,551,060 B2 | 10/2013 | Schuessler et al. | |
| 8,568,386 B2 | 10/2013 | Malhi | |
| 8,679,081 B2 | 3/2014 | Heagle et al. | |
| 8,834,451 B2 | 9/2014 | Blott et al. | |
| 8,926,592 B2 | 1/2015 | Blott et al. | |
| 9,017,302 B2 | 4/2015 | Vitaris et al. | |
| 9,198,801 B2 | 12/2015 | Weston | |
| 9,211,365 B2 | 12/2015 | Weston | |
| 9,289,542 B2 | 3/2016 | Blott et al. | |
| 2002/0077661 A1 | 6/2002 | Saadat | |
| 2002/0115951 A1 | 8/2002 | Norstrem et al. | |
| 2002/0120185 A1 | 8/2002 | Johnson | |
| 2002/0143286 A1 | 10/2002 | Tumey | |
| 2002/0193752 A1 * | 12/2002 | Lynn | A61B 10/0045 604/249 |
| 2008/0035677 A1 * | 2/2008 | Daansen | B05B 11/007 222/310 |
| 2012/0016213 A1 | 1/2012 | Burkholz | |
| 2012/0129186 A1 | 5/2012 | Garcia et al. | |
| 2012/0150068 A1 | 6/2012 | Cucin | |
| 2014/0163491 A1 | 6/2014 | Schuessler et al. | |
| 2015/0080788 A1 | 3/2015 | Blott et al. | |
| 2016/0000364 A1 | 1/2016 | Mendels et al. | |
| 2017/0037703 A1 * | 2/2017 | le Roux | E21B 21/10 |

FOREIGN PATENT DOCUMENTS

| | | |
|---|---|---|
| AU | 755496 B2 | 12/2002 |
| CA | 2005436 A1 | 6/1990 |
| DE | 26 40 413 A1 | 3/1978 |
| DE | 43 06 478 A1 | 9/1994 |
| DE | 29 504 378 U1 | 9/1995 |
| EP | 0100148 A1 | 2/1984 |

(56) References Cited

FOREIGN PATENT DOCUMENTS

| | | |
|---|---|---|
| EP | 0117632 A2 | 9/1984 |
| EP | 0161865 A2 | 11/1985 |
| EP | 0358302 A2 | 3/1990 |
| EP | 1018967 A1 | 7/2000 |
| GB | 692578 A | 6/1953 |
| GB | 2 195 255 A | 4/1988 |
| GB | 2 197 789 A | 6/1988 |
| GB | 2 220 357 A | 1/1990 |
| GB | 2 235 877 A | 3/1991 |
| GB | 2 329 127 A | 3/1999 |
| GB | 2 333 965 A | 8/1999 |
| JP | 4129536 B2 | 8/2008 |
| SG | 71559 | 4/2002 |
| WO | 80/02182 A1 | 10/1980 |
| WO | 87/04626 A1 | 8/1987 |
| WO | 90/010424 A1 | 9/1990 |
| WO | 93/009727 A1 | 5/1993 |
| WO | 9415665 A1 | 7/1994 |
| WO | 94/020041 A1 | 9/1994 |
| WO | 96/05873 A1 | 2/1996 |
| WO | 97/18007 A1 | 5/1997 |
| WO | 99/13793 A1 | 3/1999 |
| WO | 0124707 A1 | 4/2001 |

OTHER PUBLICATIONS

Susan Mendez-Eatmen, RN; "When wounds Won't Heal" RN Jan. 1998, vol. 61 (1); Medical Economics Company, Inc., Montvale, NJ, USA; pp. 20-24.

James H. Blackburn II, MD et al.: Negative-Pressure Dressings as a Bolster for Skin Grafts; Annals of Plastic Surgery, vol. 40, No. 5, May 1998, pp. 453-457; Lippincott Williams & Wilkins, Inc., Philidelphia, PA, USA.

John Masters; "Reliable, Inexpensive and Simple Suction Dressings"; Letter to the Editor, British Journal of Plastic Surgery, 1998, vol. 51 (3), p. 267; Elsevier Science/The British Association of Plastic Surgeons, UK.

S.E. Greer, et al. "The Use of Subatmospheric Pressure Dressing Therapy to Close Lymphocutaneous Fistulas of the Groin" British Journal of Plastic Surgery (2000), 53, pp. 484-487.

George V. Letsou, MD., et al.; "Stimulation of Adenylate Cyclase Activity in Cultured Endothelial Cells Subjected to Cyclic Stretch"; Journal of Cardiovascular Surgery, 31, 1990, pp. 634-639.

Orringer, Jay, et al; "Management of Wounds in Patients with Complex Enterocutaneous Fistulas"; Surgery, Gynecology & Obstetrics, Jul. 1987, vol. 165, pp. 79-80.

International Search Report for PCT International Application PCT/GB95/01983; dated Nov. 23, 1995.

PCT International Search Report for PCT International Application PCT/GB98/02713; dated Jan. 8, 1999.

PCT Written Opinion; PCT International Application PCT/GB98/02713; dated Jun. 8, 1999.

PCT International Examination and Search Report, PCT International Application PCT/GB96/02802; dated Jan. 15, 1998 & Apr. 29, 1997.

PCT Written Opinion, PCT International Application PCT/GB96/02802; dated Sep. 3, 1997.

Dattilo, Philip P., Jr., et al; "Medical Textiles: Application of an Absorbable Barbed Bi-directional Surgical Suture"; Journal of Textile and Apparel, Technology and Management, vol. 2, Issue 2, Spring 2002, pp. 1-5.

Kostyuchenok, B.M., et al; "Vacuum Treatment in the Surgical Management of Purulent Wounds"; Vestnik Khirurgi, Sep. 1986, pp. 18-21 and 6 page English translation thereof.

Davydov, Yu. A., et al; "Vacuum Therapy in the Treatment of Purulent Lactation Mastitis"; Vestnik Khirurgi, May 14, 1986, pp. 66-70, and 9 page English translation thereof.

Yusupov. Yu.N., et al; "Active Wound Drainage", Vestnki Khirurgi, vol. 138, Issue 4, 1987, and 7 page English translation thereof.

Davydov, Yu.A., et al; "Bacteriological and Cytological Assessment of Vacuum Therapy for Purulent Wounds"; Vestnik Khirugi, Oct. 1988, pp. 48-52, and 8 page English translation thereof.

Davydov, Yu.A., et al; "Concepts for the Clinical-Biological Management of the Wound Process in the Treatment of Purulent Wounds by Means of Vacuum Therapy"; Vestnik Khirurgi, Jul. 7, 1980, pp. 132-136, and 8 page English translation thereof.

Chariker, Mark E., M.D., et al; "Effective Management of incisional and cutaneous fistulae with closed suction wound drainage"; Contemporary Surgery, vol. 34, Jun. 1989, pp. 59-63.

Egnell Minor, Instruction Book, First Edition, 300 7502, Feb. 1975, pp. 24.

Egnell Minor: Addition to the Users Manual Concerning Overflow Protection—Concerns all Egnell Pumps, Feb. 3, 1983, pp. 2.

Svedman, P.: "Irrigation Treatment of Leg Ulcers", The Lancet, Sep. 3, 1983, pp. 532-534.

Chinn, Steven D. et al.: "Closed Wound Suction Drainage", The Journal of Foot Surgery, vol. 24, No. 1, 1985, pp. 76-81.

Arnljots, Björn et al.: "Irrigation Treatment in Split-Thickness Skin Grafting of Intractable Leg Ulcers", Scand J. Plast Reconstr. Surg., No. 19, 1985, pp. 211-213.

Svedman, P.: "A Dressing Allowing Continuous Treatment of a Biosurface", IRCS Medical Science: Biomedical Technology, Clinical Medicine, Surgery and Transplantation, vol. 7, 1979, p. 221.

Svedman, P. et al: "A Dressing System Providing Fluid Supply and Suction Drainage Used for Continuous of Intermittent Irrigation", Annals of Plastic Surgery, vol. 17, No. 2, Aug. 1986, pp. 125-133.

N.A. Bagautdinov, "Variant of External Vacuum Aspiration in the Treatment of Purulent Diseases of Soft Tissues," Current Problems in Modern Clinical Surgery: Interdepartmental Collection, edited by V. Ye Volkov et al. (Chuvashia State University, Cheboksary, U.S.S.R. 1986); pp. 94-96 (certified translation).

K.F. Jeter, T.E. Tintle, and M. Chariker, "Managing Draining Wounds and Fistulae: New and Established Methods," Chronic Wound Care, edited by D. Krasner (Health Management Publications, Inc., King of Prussia, PA 1990), pp. 240-246.

G. Živadinovi?, V. ?uki?, Ž. Maksimovi?, ?. Radak, and P. Peška, "Vacuum Therapy in the Treatment of Peripheral Blood Vessels," Timok Medical Journal 11 (1986), pp. 161-164 (certified translation).

F.E. Johnson, "An Improved Technique for Skin Graft Placement Using a Suction Drain," Surgery, Gynecology, and Obstetrics 159 (1984), pp. 584-585.

A.A. Safronov, Dissertation Abstract, Vacuum Therapy of Trophic Ulcers of the Lower Leg with Simultaneous Autoplasty of the Skin (Central Scientific Research Institute of Traumatology and Orthopedics, Moscow, U.S.S.R. 1967) (certified translation).

M. Schein, R. Saadia, J.R. Jamieson, and G.A.G. Decker, "The 'Sandwich Technique' in the Management of the Open Abdomen," British Journal of Surgery 73 (1986), pp. 369-370.

D.E. Tribble, An Improved Sump Drain-Irrigation Device of Simple Construction, Archives of Surgery 105 (1972) pp. 511-513.

M.J. Morykwas, L.C. Argenta, E.I. Shelton-Brown, and W. McGuirt, "Vacuum-Assisted Closure: A New Method for Wound Control and Treatment: Animal Studies and Basic Foundation," Annals of Plastic Surgery 38 (1997), pp. 553-562 (Morykwas I).

C.E. Tennants, "The Use of Hypermia in the Postoperative Treatment of Lesions of the Extremities and Thorax," Journal of the American Medical Association 64 (1915), pp. 1548-1549.

Selections from W. Meyer and V. Schmieden, Bier's Hyperemic Treatment in Surgery, Medicine, and the Specialties: A Manual of Its Practical Application, (W.B. Saunders Co., Philadelphia, PA 1909), pp. 17-25, 44-64, 90-96, 167-170, and 210-211.

V.A. Solovev et al., Guidelines, The Method of Treatment of Immature External Fistulas in the Upper Gastrointestinal Tract, editor-in-chief Prov. V.I. Parahonyak (S.M. Kirov Gorky State Medical Institute, Gorky, U.S.S.R. 1987) ("Solovev Guidelines").

V.A. Kuznetsov & N.a. Bagautdinov, "Vacuum and Vacuum-Sorption Treatment of Open Septic Wounds," in II All-Union Conference on Wounds and Wound Infections: Presentation Abstracts, edited by B.M. Kostyuchenok et al. (Moscow, U.S.S.R. Oct. 28-29, 1986) pp. 91-92 ("Bagautdinov II").

(56) References Cited

OTHER PUBLICATIONS

V.A. Solovev, Dissertation Abstract, Treatment and Prevention of Suture Failures after Gastric Resection (S.M. Kirov Gorky State Medical Institute, Gorky, U.S.S.R. 1988) ("Solovev Abstract").
V.A.C.® Therapy Clinical Guidelines: A Reference Source for Clinicians; Jul. 2007.
International Search Report and Written Opinion for corresponding Application No. PCT/US2017/046265, dated Jan. 4, 2018.

* cited by examiner

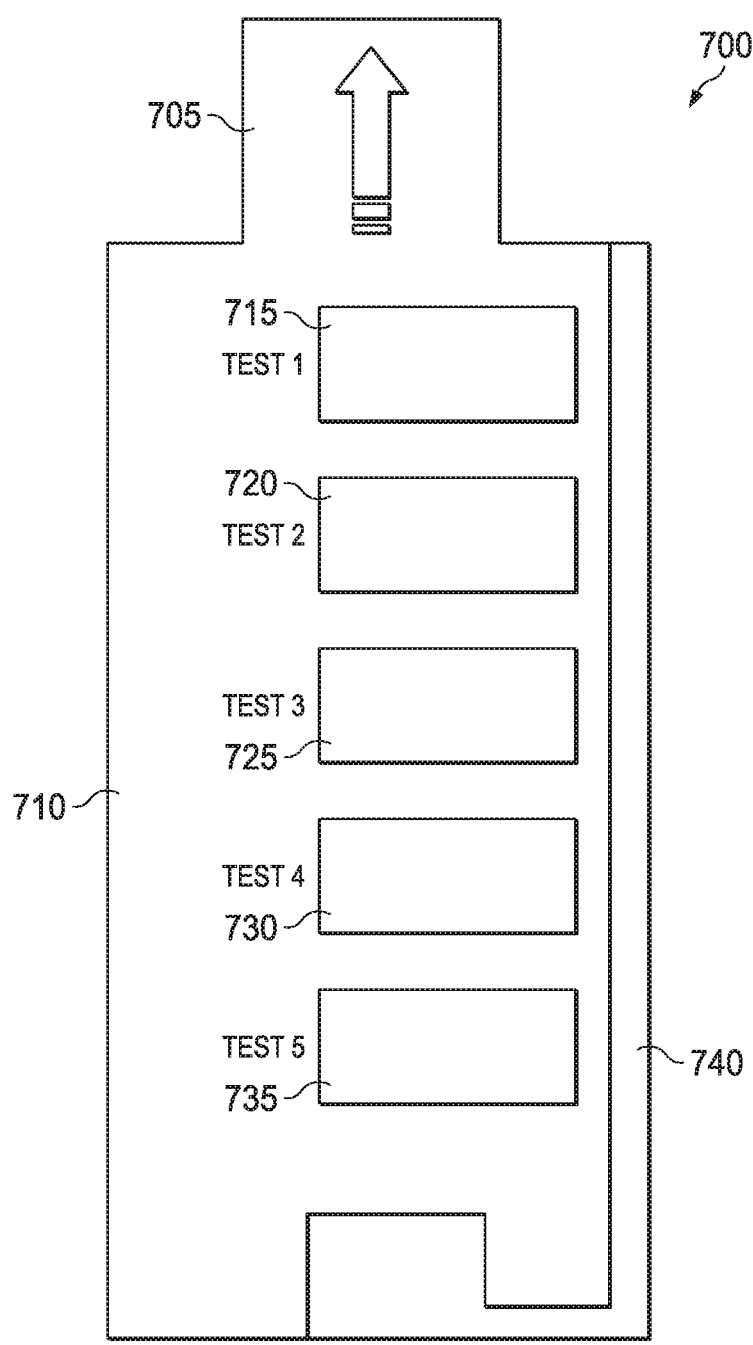
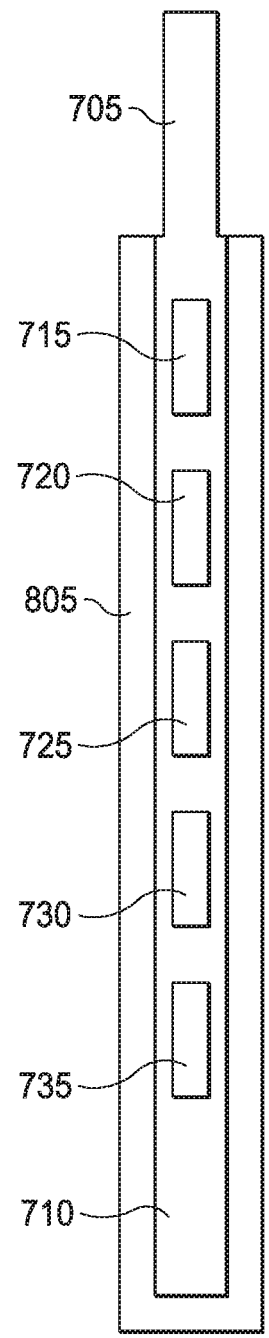
FIG. 7
FIG. 8

IN-LINE DIAGNOSTIC TOOL FOR NEGATIVE-PRESSURE THERAPY

RELATED APPLICATION

This application claims the benefit, under 35 USC § 119(e), of the filing of U.S. Provisional Patent Application Ser. No. 62/376,645, entitled "In-Line Diagnostic Tool For Negative-Pressure Therapy" filed Aug. 18, 2016, which is incorporated herein by reference for all purposes.

TECHNICAL FIELD

The invention set forth in the appended claims relates generally to tissue treatment systems and more particularly, but without limitation, to apparatuses and methods for in-line diagnostics of fluid in negative-pressure treatment of tissue.

BACKGROUND

Clinical studies and practice have shown that reducing pressure in proximity to a tissue site can augment and accelerate growth of new tissue at the tissue site. The applications of this phenomenon are numerous, but it has proven particularly advantageous for treating wounds. Regardless of the etiology of a wound, whether trauma, surgery, or another cause, proper care of the wound is important to the outcome. Treatment of wounds or other tissue with reduced pressure may be commonly referred to as "negative-pressure therapy," but is also known by other names, including "negative-pressure wound therapy," "reduced-pressure therapy," "vacuum therapy," "vacuum-assisted closure," and "topical negative-pressure," for example. Negative-pressure therapy may provide a number of benefits, including migration of epithelial and subcutaneous tissues, improved blood flow, and micro-deformation of tissue at a wound site. Together, these benefits can increase development of granulation tissue and reduce healing times.

There is also widespread acceptance that cleansing a tissue site can be highly beneficial for new tissue growth. For example, a wound can be washed out with a stream of liquid solution, or a cavity can be washed out using a liquid solution for therapeutic purposes. These practices are commonly referred to as "irrigation" and "lavage" respectively. "Instillation" is another practice that generally refers to a process of slowly introducing fluid to a tissue site and leaving the fluid for a prescribed period of time before removing the fluid. For example, instillation of topical treatment solutions over a wound bed can be combined with negative-pressure therapy to further promote wound healing by loosening soluble contaminants in a wound bed and removing infectious material. As a result, soluble bacterial burden can be decreased, contaminants removed, and the wound cleansed.

While the clinical benefits of negative-pressure therapy and instillation therapy are widely known, improvements to therapy systems, components, and processes may benefit healthcare providers and patients.

BRIEF SUMMARY

New and useful systems, apparatuses, and methods for sampling fluid in a negative-pressure therapy environment are set forth in the appended claims. Illustrative embodiments are also provided to enable a person skilled in the art to make and use the claimed subject matter.

For example, in some embodiments, an in-line diagnostic system can facilitate the sampling, testing, and measurement of various biomarkers, aiding in the determination of therapy efficacy, wound status, and infection detection, without disrupting therapy. In some embodiments, a system may comprise an in-line sampling interface and one or more disposable test media.

For example, an in-line sampling interface may comprise a housing that may be integrated with or configured to be coupled to fluid conductors in a fluid path between a tissue site and a negative-pressure source. In operation, fluid may flow from a tissue site through the housing toward the negative-pressure source. In some embodiments, the housing may be integrating with or coupled to a dressing interface or a fluid container. The sampling interface preferably comprises features for minimizing cross-contamination between samples or tests. For example, the interface may shield or divert exudate to minimize collateral or accidental exposure to components other than test media.

In some embodiments, one or more of the test media may be disposed in or on a substrate, such as a disposable fluid sampling insert or a test strip. A suitable substrate may comprise a hydrophilic wicking material, hydrophobic wicking material with a hydrophilic treatment such as adhesive patterning, or a combination of both. The substrate may comprise a multi-layer strip configured to wick or otherwise direct a fluid sample to one or more of the test media. Some embodiments may also include a progress indicator, such as a color change (chromatic), a fill bar, or other conformational change to indicate that a sufficient sample has been collected or a suitable exposure time has been reached.

A test medium may comprise a consumable element configured to test one or more constituents of a fluid, which may vary according to diagnostic need or requirement. In some embodiments, a test medium may be capable of indicating a concentration of a specific enzyme, metabolite, or protein. For example, some embodiments of a test medium may be used for monitoring wound progression by indicating the concentration of certain matrix metalloproteinases or tissue inhibitors of metalloproteinases. Additionally or alternatively, a test medium may be used for detecting the presence of infection by indicating the concentration of certain pro-inflammatory and anti-inflammatory cytokines.

More generally, a sampling interface apparatus may comprise an inlet port, an outlet port, and a sampling chamber fluidly coupled to the inlet port and to the outlet port. The apparatus may also comprise a sampling port and at least one split seal disposed between the sampling port and the sampling chamber. The sampling port may be configured to provide access to the sampling chamber. The split seal may comprise more than one sealing member, and preferably comprises at least two sealing members. For example, a first sealing member and a second sealing member may converge to a sealing line in some embodiments. In more specific examples, a first sealing member may abut a second sealing member to form a sealing line.

In some embodiments, a split seal may comprise a first external surface and a second external surface that converge to form a sealing line. The first external surface and the second external surface may be convex in some embodiments, and may converge to a sealing line at an angle that is less than or equal to a straight angle, and greater than or equal to a zero angle.

The apparatus may additionally include at least one fluid collection channel disposed interior to the split seal. For example, a fluid collection channel may be formed by a concave interior surface of the split seal.

In general, a lateral flow strip for sampling fluid removed from a tissue site may comprise an acquisition surface and a migration medium fluidly coupled to the acquisition surface. At least one test medium may be fluidly coupled to the migration medium, and a liquid-impermeable cover may enclose the migration medium and the test medium. The acquisition surface is preferably not enclosed. In some embodiments, the lateral flow strip may additionally comprise a progress indicator adapted to be activated by the fluid.

A lateral flow strip is preferably suitable for use with a sampling interface. For example, a lateral flow strip may comprise an acquisition surface configured to be inserted through a sampling port to acquire fluid from a sampling chamber. In some embodiments a lateral flow strip and a sampling interface may be provided as a diagnostic kit.

In other aspects, a sampling interface for collecting fluid on a lateral flow strip may comprise a primary split seal with an internal fluid collection channel and at least one external surface adapted to remove excess fluid from the lateral flow strip and direct the excess fluid into the fluid collection channel. A secondary split seal may be adapted to stabilize the lateral flow strip.

Objectives, advantages, and a preferred mode of making and using the claimed subject matter may be understood best by reference to the accompanying drawings in conjunction with the following detailed description of illustrative embodiments.

BRIEF DESCRIPTION OF THE DRAWINGS

FIG. 7 is a schematic diagram of an example of a lateral flow strip that may be associated with some embodiments of the sampling interface of FIG. 2 for sampling fluid;

FIG. 8 is a schematic cross section of an example embodiment of the lateral flow strip of FIG. 7;

DESCRIPTION OF EXAMPLE EMBODIMENTS

The following description of example embodiments provides information that enables a person skilled in the art to make and use the subject matter set forth in the appended claims, but may omit certain details already well-known in the art. The following detailed description is, therefore, to be taken as illustrative and not limiting.

The example embodiments may also be described herein with reference to spatial relationships between various elements or to the spatial orientation of various elements depicted in the attached drawings. In general, such relationships or orientation assume a frame of reference consistent with or relative to a patient in a position to receive treatment. However, as should be recognized by those skilled in the art, this frame of reference is merely a descriptive expedient rather than a strict prescription.

Figure 1:
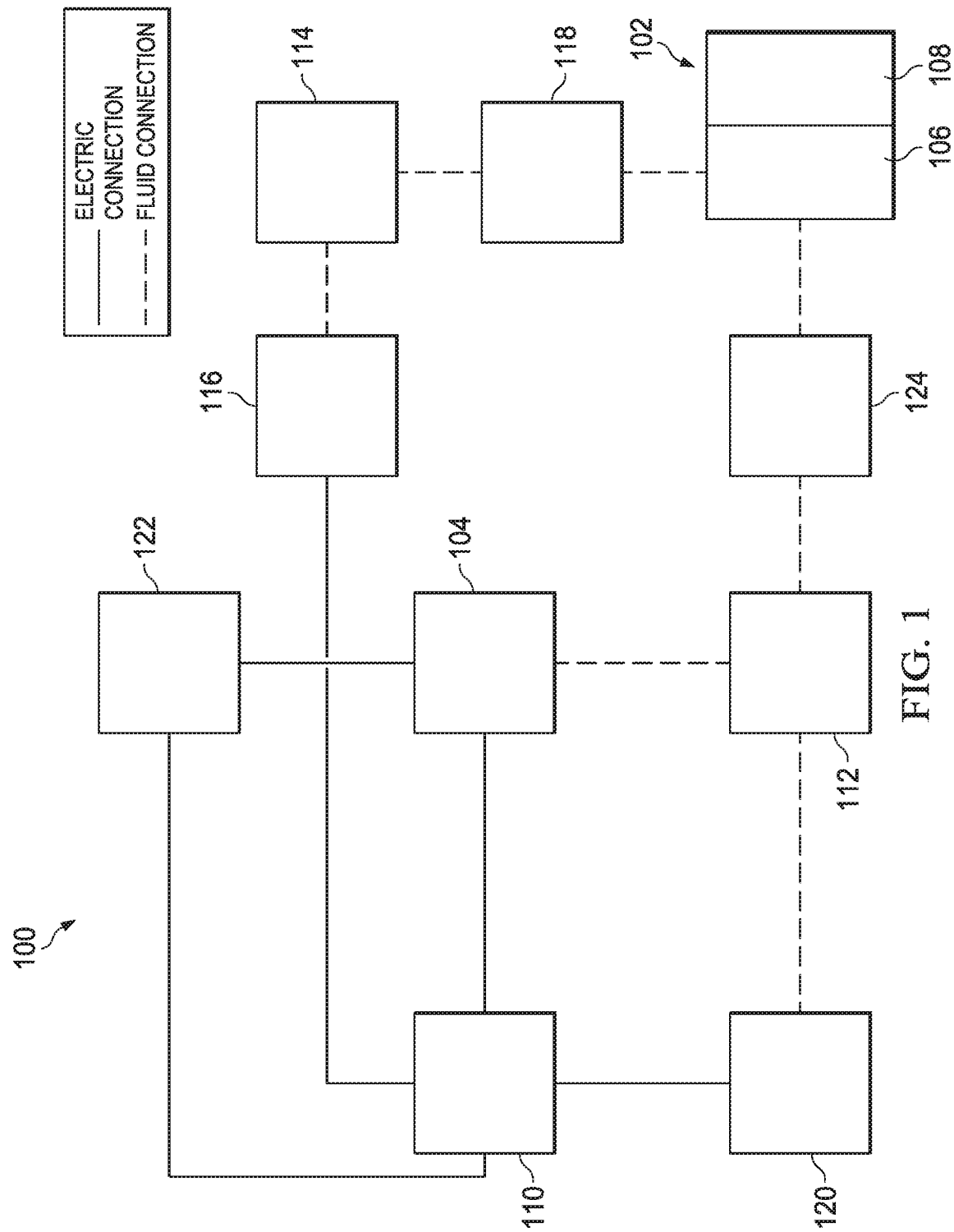
FIG. 1 is a functional block diagram of an example embodiment of a therapy system that can provide negative-pressure therapy with instillation of topical treatment solution in accordance with this specification.

FIG. 1 is a simplified functional block diagram of an example embodiment of a therapy system 100 that can provide negative-pressure therapy with instillation of topical treatment solution to a tissue site in accordance with this specification.

The term "tissue site" in this context broadly refers to a wound, defect, or other treatment target located on or within tissue, including but not limited to, bone tissue, adipose tissue, muscle tissue, neural tissue, dermal tissue, vascular tissue, connective tissue, cartilage, tendons, or ligaments. A wound may include chronic, acute, traumatic, subacute, and dehisced wounds, partial-thickness burns, ulcers (such as diabetic, pressure, or venous insufficiency ulcers), flaps, and grafts, for example. The term "tissue site" may also refer to areas of any tissue that are not necessarily wounded or defective, but are instead areas in which it may be desirable to add or promote the growth of additional tissue. For example, negative pressure may be applied to a tissue site to grow additional tissue that may be harvested and transplanted.

The therapy system 100 may include negative-pressure supply, and may include or be configured to be coupled to a distribution component, such as a dressing. In general, a distribution component may refer to any complementary or ancillary component configured to be fluidly coupled to a negative-pressure supply in a fluid path between a negative-pressure supply and a tissue site. A distribution component is preferably detachable, and may be disposable, reusable, or recyclable. For example, a dressing 102 may be fluidly coupled to a negative-pressure source 104, as illustrated in FIG. 1. A dressing may include a cover, a tissue interface, or both in some embodiments. The dressing 102, for example, may include a cover 106 and a tissue interface 108. A regulator or a controller, such as a controller 110, may also be coupled to the negative-pressure source 104.

In some embodiments, a dressing interface may facilitate coupling the negative-pressure source 104 to the dressing 102. For example, such a dressing interface may be a T.R.A.C. pad or SENSAT.R.A.C. pad available from KCI of San Antonio, Tex. The therapy system 100 may optionally include a fluid container, such as a container 112, coupled to the dressing 102 and to the negative-pressure source 104.

The therapy system 100 may also include a source of instillation solution. For example, a solution source 114 may be fluidly coupled to the dressing 102, as illustrated in the example embodiment of FIG. 1. The solution source 114 may be fluidly coupled to a positive-pressure source such as the positive-pressure source 116 in some embodiments, or may be fluidly coupled to the negative-pressure source 104. A regulator, such as an instillation regulator 118, may also be fluidly coupled to the solution source 114 and the dressing 102. In some embodiments, the instillation regulator 118 may also be fluidly coupled to the negative-pressure source 104 through the dressing 102, as illustrated in the example of FIG. 1.

Additionally, the therapy system 100 may include sensors to measure operating parameters and provide feedback signals to the controller 110 indicative of the operating parameters. As illustrated in FIG. 1, for example, the therapy system 100 may include a pressure sensor 120, an electric sensor 122, or both, coupled to the controller 110. The pressure sensor 120 may also be coupled or configured to be coupled to a distribution component and to the negative-pressure source 104.

The therapy system 100 may additionally include an apparatus for sampling fluid removed from a tissue site, such as a sampling interface 124 disposed in-line between the dressing 102 and the negative-pressure source 104. For example, the sampling interface 124 may be disposed between the dressing 102 and the container 112 as illustrated in FIG. 1. In other examples, the sampling interface 124 may be integral to the container 112 or a dressing interface.

Components may be fluidly coupled to each other to provide a path for transferring fluids (i.e., liquid and/or gas) between the components. For example, components may be fluidly coupled through a fluid conductor, such as a tube. A "tube," as used herein, broadly includes a tube, pipe, hose, conduit, or other structure with one or more lumina adapted to convey a fluid between two ends. Typically, a tube is an elongated, cylindrical structure with some flexibility, but the geometry and rigidity may vary. In some embodiments, components may also be coupled by virtue of physical proximity, being integral to a single structure, or being formed from the same piece of material. Moreover, some fluid conductors may be molded into or otherwise integrally combined with other components. Coupling may also include mechanical, thermal, electrical, or chemical coupling (such as a chemical bond) in some contexts. For example, a tube may mechanically and fluidly couple the dressing 102 to the container 112 in some embodiments.

In general, components of the therapy system 100 may be coupled directly or indirectly. For example, the negative-pressure source 104 may be directly coupled to the controller 110, and may be indirectly coupled to the dressing 102 through the container 112.

The fluid mechanics of using a negative-pressure source to reduce pressure in another component or location, such as within a sealed therapeutic environment, can be mathematically complex. However, the basic principles of fluid mechanics applicable to negative-pressure therapy and instillation are generally well-known to those skilled in the art, and the process of reducing pressure may be described illustratively herein as "delivering," "distributing," or "generating" negative pressure, for example.

In general, exudates and other fluids flow toward lower pressure along a fluid path. Thus, the term "downstream" typically implies something in a fluid path relatively closer to a source of negative pressure or further away from a source of positive pressure. Conversely, the term "upstream" implies something relatively further away from a source of negative pressure or closer to a source of positive pressure. Similarly, it may be convenient to describe certain features in terms of fluid "inlet" or "outlet" in such a frame of reference. This orientation is generally presumed for purposes of describing various features and components herein. However, the fluid path may also be reversed in some applications (such as by substituting a positive-pressure source for a negative-pressure source) and this descriptive convention should not be construed as a limiting convention.

"Negative pressure" generally refers to a pressure less than a local ambient pressure, such as the ambient pressure in a local environment external to a sealed therapeutic environment provided by the dressing 102. In many cases, the local ambient pressure may also be the atmospheric pressure at which a tissue site is located. Alternatively, the pressure may be less than a hydrostatic pressure associated with tissue at the tissue site. Unless otherwise indicated, values of pressure stated herein are gauge pressures. Similarly, references to increases in negative pressure typically refer to a decrease in absolute pressure, while decreases in negative pressure typically refer to an increase in absolute pressure. While the amount and nature of negative pressure applied to a tissue site may vary according to therapeutic requirements, the pressure is generally a low vacuum, also commonly referred to as a rough vacuum, between −5 mm Hg (−667 Pa) and −500 mm Hg (−66.7 kPa). Common therapeutic ranges are between −75 mm Hg (−9.9 kPa) and −300 mm Hg (−39.9 kPa).

A negative-pressure supply, such as the negative-pressure source 104, may be a reservoir of air at a negative pressure, or may be a manual or electrically-powered device that can reduce the pressure in a sealed volume, such as a vacuum pump, a suction pump, a wall suction port available at many healthcare facilities, or a micro-pump, for example. A negative-pressure supply may be housed within or used in conjunction with other components, such as sensors, processing units, alarm indicators, memory, databases, software, display devices, or user interfaces that further facilitate therapy. For example, in some embodiments, the negative-pressure source 104 may be combined with the controller 110 and other components into a therapy unit. A negative-pressure supply may also have one or more supply ports configured to facilitate coupling and de-coupling the negative-pressure supply to one or more distribution components.

The tissue interface 108 can be generally adapted to contact a tissue site. The tissue interface 108 may be partially or fully in contact with the tissue site. If the tissue site is a wound, for example, the tissue interface 108 may partially or completely fill the wound, or may be placed over the wound. The tissue interface 108 may take many forms, and may have many sizes, shapes, or thicknesses depending on a variety of factors, such as the type of treatment being implemented or the nature and size of a tissue site. For example, the size and shape of the tissue interface 108 may be adapted to the contours of deep and irregular shaped tissue sites. Moreover, any or all of the surfaces of the tissue interface 108 may have projections or an uneven, course, or jagged profile that can induce strains and stresses on a tissue site, which can promote granulation at the tissue site.

In some embodiments, the tissue interface 108 may be a manifold. A "manifold" in this context generally includes any substance or structure providing a plurality of pathways adapted to collect or distribute fluid across a tissue site under pressure. For example, a manifold may be adapted to receive negative pressure from a source and distribute negative pressure through multiple apertures across a tissue site, which may have the effect of collecting fluid from across a tissue site and drawing the fluid toward the source. In some embodiments, the fluid path may be reversed or a secondary fluid path may be provided to facilitate delivering fluid across a tissue site.

In some illustrative embodiments, the pathways of a manifold may be interconnected to improve distribution or collection of fluids across a tissue site. In some illustrative embodiments, a manifold may be a porous foam material having interconnected cells or pores. For example, cellular foam, open-cell foam, reticulated foam, porous tissue collections, and other porous material such as gauze or felted mat generally include pores, edges, and/or walls adapted to form interconnected fluid channels. Liquids, gels, and other foams may also include or be cured to include apertures and fluid pathways. In some embodiments, a manifold may additionally or alternatively comprise projections that form interconnected fluid pathways. For example, a manifold may be molded to provide surface projections that define interconnected fluid pathways.

The average pore size of a foam may vary according to needs of a prescribed therapy. For example, in some embodiments, the tissue interface 108 may be a foam having pore sizes in a range of 400-600 microns. The tensile strength of the tissue interface 108 may also vary according to needs of a prescribed therapy. For example, the tensile strength of a foam may be increased for instillation of topical treatment solutions. In one non-limiting example, the tissue interface 108 may be an open-cell, reticulated polyurethane foam such as GRANUFOAM dressing or V.A.C. VERAFLO dressing, both available from Kinetic Concepts, Inc. of San Antonio, Tex.

The tissue interface 108 may be either hydrophobic or hydrophilic. In an example in which the tissue interface 108 may be hydrophilic, the tissue interface 108 may also wick fluid away from a tissue site, while continuing to distribute negative pressure to the tissue site. The wicking properties of the tissue interface 108 may draw fluid away from a tissue site by capillary flow or other wicking mechanisms. An example of a hydrophilic foam is a polyvinyl alcohol, open-cell foam such as V.A.C. WHITEFOAM dressing available from Kinetic Concepts, Inc. of San Antonio, Tex. Other hydrophilic foams may include those made from polyether. Other foams that may exhibit hydrophilic characteristics include hydrophobic foams that have been treated or coated to provide hydrophilicity.

The tissue interface 108 may further promote granulation at a tissue site when pressure within the sealed therapeutic environment is reduced. For example, any or all of the surfaces of the tissue interface 108 may have an uneven, coarse, or jagged profile that can induce microstrains and stresses at a tissue site if negative pressure is applied through the tissue interface 108.

In some embodiments, the tissue interface 108 may be constructed from bioresorbable materials. Suitable bioresorbable materials may include, without limitation, a polymeric blend of polylactic acid (PLA) and polyglycolic acid (PGA). The polymeric blend may also include without limitation polycarbonates, polyfumarates, and capralactones. The tissue interface 108 may further serve as a scaffold for new cell-growth, or a scaffold material may be used in conjunction with the tissue interface 108 to promote cell-growth. A scaffold is generally a substance or structure used to enhance or promote the growth of cells or formation of tissue, such as a three-dimensional porous structure that provides a template for cell growth. Illustrative examples of scaffold materials include calcium phosphate, collagen, PLA/PGA, coral hydroxy apatites, carbonates, or processed allograft materials.

In some embodiments, the cover 106 may provide a bacterial bather and protection from physical trauma. The cover 106 may also be constructed from a material that can reduce evaporative losses and provide a fluid seal between two components or two environments, such as between a therapeutic environment and a local external environment. The cover 106 may be, for example, an elastomeric film or membrane that can provide a seal adequate to maintain a negative pressure at a tissue site for a given negative-pressure source. The cover 106 may have a high moisture-vapor transmission rate (MVTR) in some applications. For example, the MVTR may be at least 300 g/m^2 per twenty-four hours in some embodiments. In some example embodiments, the cover 106 may be a polymer drape, such as a polyurethane film, that is permeable to water vapor but impermeable to liquid. Such drapes typically have a thickness in the range of 25-50 microns. For permeable materials, the permeability generally should be low enough that a desired negative pressure may be maintained.

An attachment device may be used to attach the cover 106 to an attachment surface, such as undamaged epidermis, a gasket, or another cover. The attachment device may take many forms. For example, an attachment device may be a medically-acceptable, pressure-sensitive adhesive that extends about a periphery, a portion, or an entire sealing member. In some embodiments, for example, some or all of the cover 106 may be coated with an acrylic adhesive having a coating weight between 25-65 grams per square meter (g.s.m.). Thicker adhesives, or combinations of adhesives, may be applied in some embodiments to improve the seal and reduce leaks. Other example embodiments of an attachment device may include a double-sided tape, paste, hydrocolloid, hydrogel, silicone gel, or organogel.

A controller, such as the controller 110, may be a microprocessor or computer programmed to operate one or more components of the therapy system 100, such as the negative-pressure source 104. In some embodiments, for example, the controller 110 may be a microcontroller, which generally comprises an integrated circuit containing a processor core and a memory programmed to directly or indirectly control one or more operating parameters of the therapy system 100. Operating parameters may include the power applied to the negative-pressure source 104, the pressure generated by the negative-pressure source 104, or the pressure distributed to the tissue interface 108, for example. The controller 110 is also preferably configured to receive one or more input signals, such as a feedback signal, and programmed to modify one or more operating parameters based on the input signals.

Sensors, such as the pressure sensor 120 or the electric sensor 122, are generally known in the art as any apparatus operable to detect or measure a physical phenomenon or property, and generally provide a signal indicative of the phenomenon or property that is detected or measured. For example, the pressure sensor 120 and the electric sensor 122 may be configured to measure one or more operating parameters of the therapy system 100. In some embodiments, the pressure sensor 120 may be a transducer configured to measure pressure in a pneumatic pathway and convert the measurement to a signal indicative of the pressure measured. In some embodiments, for example, the pressure sensor 120 may be a piezoresistive strain gauge. The electric sensor 122 may optionally measure operating parameters of the negative-pressure source 104, such as the voltage or current, in some embodiments. Preferably, the signals from the pressure sensor 120 and the electric sensor 122 are suitable as an input signal to the controller 110, but some signal conditioning may be appropriate in some embodiments. For example, the signal may need to be filtered or amplified before it can be processed by the controller 110. Typically, the signal is an electrical signal, but may be represented in other forms, such as an optical signal.

The container 112 is representative of a container, canister, pouch, or other storage component, which can be used to manage exudates and other fluids withdrawn from a tissue site. In many environments, a rigid container may be preferred or required for collecting, storing, and disposing of fluids. In other environments, fluids may be properly disposed of without rigid container storage, and a re-usable container could reduce waste and costs associated with negative-pressure therapy.

The solution source 114 may also be representative of a container, canister, pouch, bag, or other storage component, which can provide a solution for instillation therapy. Compositions of solutions may vary according to a prescribed therapy, but examples of solutions that may be suitable for some prescriptions include hypochlorite-based solutions, silver nitrate (0.5%), sulfur-based solutions, biguanides, cationic solutions, and isotonic solutions.

In operation, the tissue interface 108 may be placed within, over, on, or otherwise proximate to a tissue site. The cover 106 may be placed over the tissue interface 108 and sealed to an attachment surface near the tissue site. For example, the cover 106 may be sealed to undamaged epidermis peripheral to a tissue site. Thus, the dressing 102 can provide a sealed therapeutic environment proximate to a tissue site, substantially isolated from the external environment, and the negative-pressure source 104 can reduce the pressure in the sealed therapeutic environment.

Negative pressure applied across the tissue site through the tissue interface 108 in the sealed therapeutic environment can induce macrostrain and microstrain in the tissue site, as well as remove exudate and other fluid from the tissue site, which can be collected in container 112. Exudate and other fluid removed from the tissue site may also be sampled or otherwise collected through the sampling interface 124.

Figure 2:
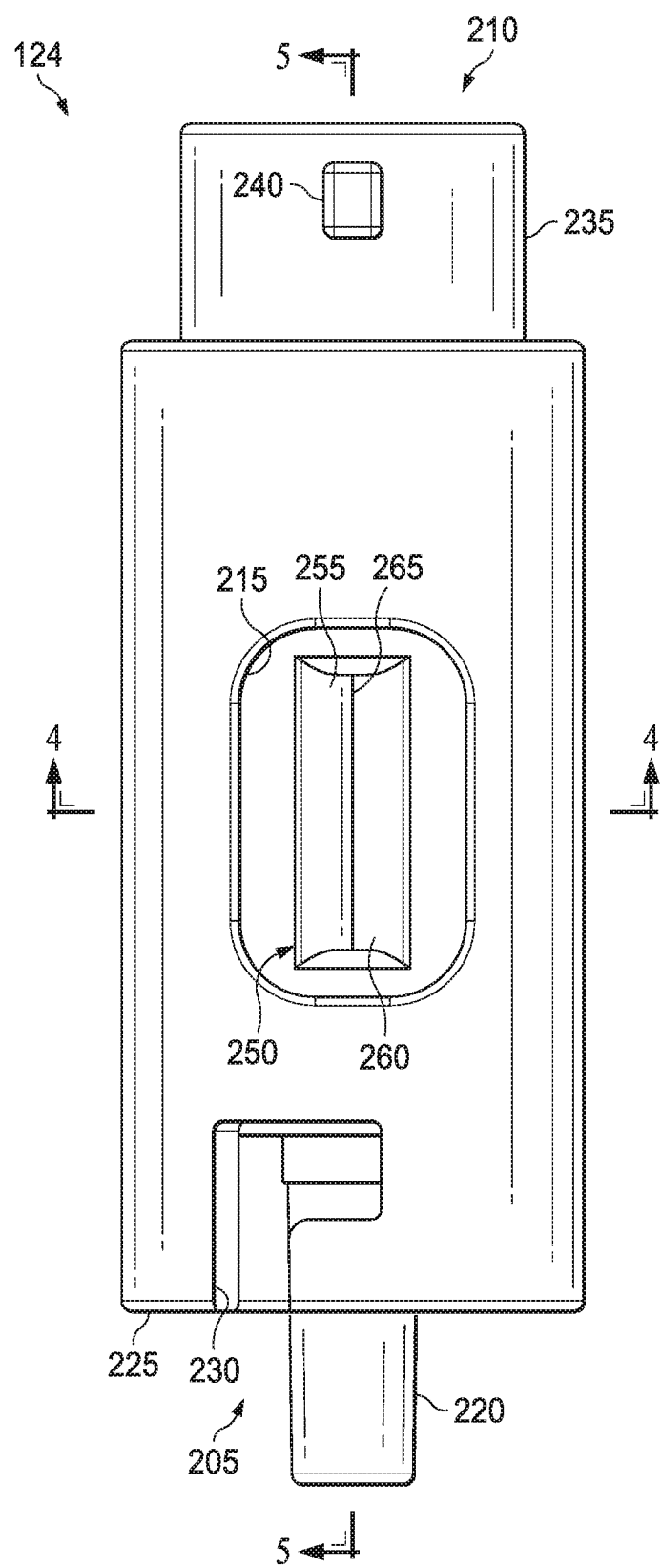
FIG. 2 is a front view of an example of a sampling interface that may be associated with some embodiments of the therapy system of FIG. 1.

FIG. 2 is a front view of an example of the sampling interface 124, illustrating additional details that may be associated with some embodiments. In the example embodiment of FIG. 2, the sampling interface 124 generally includes two fluid connectors, such as an inlet port 205 and an outlet port 210, and an aperture for sampling fluid, such as a sampling port 215. Some embodiments of the sampling interface 124 may additionally include a fitting 220, adapted to be inserted into a fluid conductor or other distribution component. In some embodiments, the two fluid connectors may comprise one or more fastening mechanisms, which can mechanically join the connectors to other distribution components. For example, as illustrated in the embodiment of FIG. 2, the inlet port 205 may comprise a female bayonet mount 225 having a slot 230 adapted to receive a lug on a compatible male bayonet mount of another distribution component. Likewise, some embodiments of the outlet port 210 may comprise a male bayonet mount 235 adapted to be inserted into a compatible female bayonet mount. For example, the bayonet mount 235 may comprise or be coupled to a lug 240, which can be configured to be inserted into a slot of a compatible female bayonet mount. Such fastening mechanisms generally allow the sampling interface 124 to be readily connected to and disconnected from other components without tools, while maintaining the integrity of the components.

A split seal 250 may also be coupled to or disposed adjacent to the sampling port 215, as illustrated in the example of FIG. 2. In some embodiments, the split seal 250 may comprise a first sealing member 255 and a second sealing member 260, which can converge to a sealing line 265.

Figure 3:
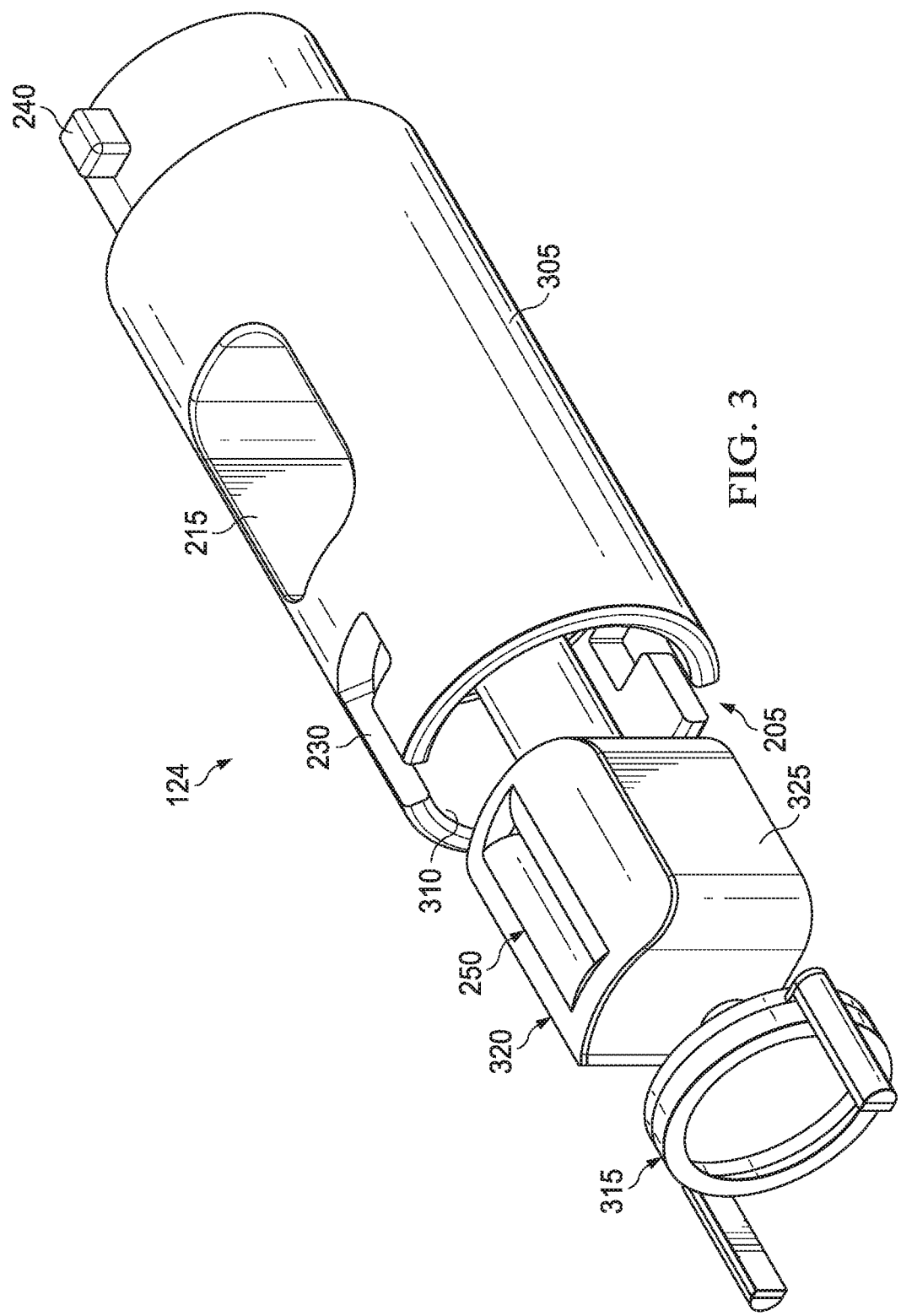
FIG. 3 is an assembly view of the sampling interface of FIG. 2.

FIG. 3 is an assembly view of the sampling interface 124 of FIG. 2, illustrating additional details that may be associated with some embodiments. For example, the sampling interface 124 may comprise a housing 305, which may be substantially cylindrical in some embodiments. The housing 305 preferably comprises or consists essentially of a material that is suitable for injection molding, and sufficiently rigid after molding to maintain its general shape under operating conditions associated with a prescribed therapy. The inlet port 205 may comprise an aperture 310 in the housing 305. A gasket 315 may be disposed in the aperture 310. For example, the gasket 315 may be a seal, such as an o-ring adapted to be disposed around the periphery of the aperture 310.

As illustrated in the example of FIG. 3, the split seal 250 may be an insert or part of an insert comprising or consisting essentially of a material that is suitable for injection molding, including overmolding or two-shot molding. Thermoplastic elastomers, such as THERMOLAST TPE from Kraiburg, may be suitable for some embodiments. Other suitable materials may include liquid silicone rubber, ethylene propylene diene monomer (M-class) rubber, or vulcanized thermoplastic, for example. In the example of FIG. 3, the split seal 250 is integral to an insert 320 having a base 325.

Figure 4:
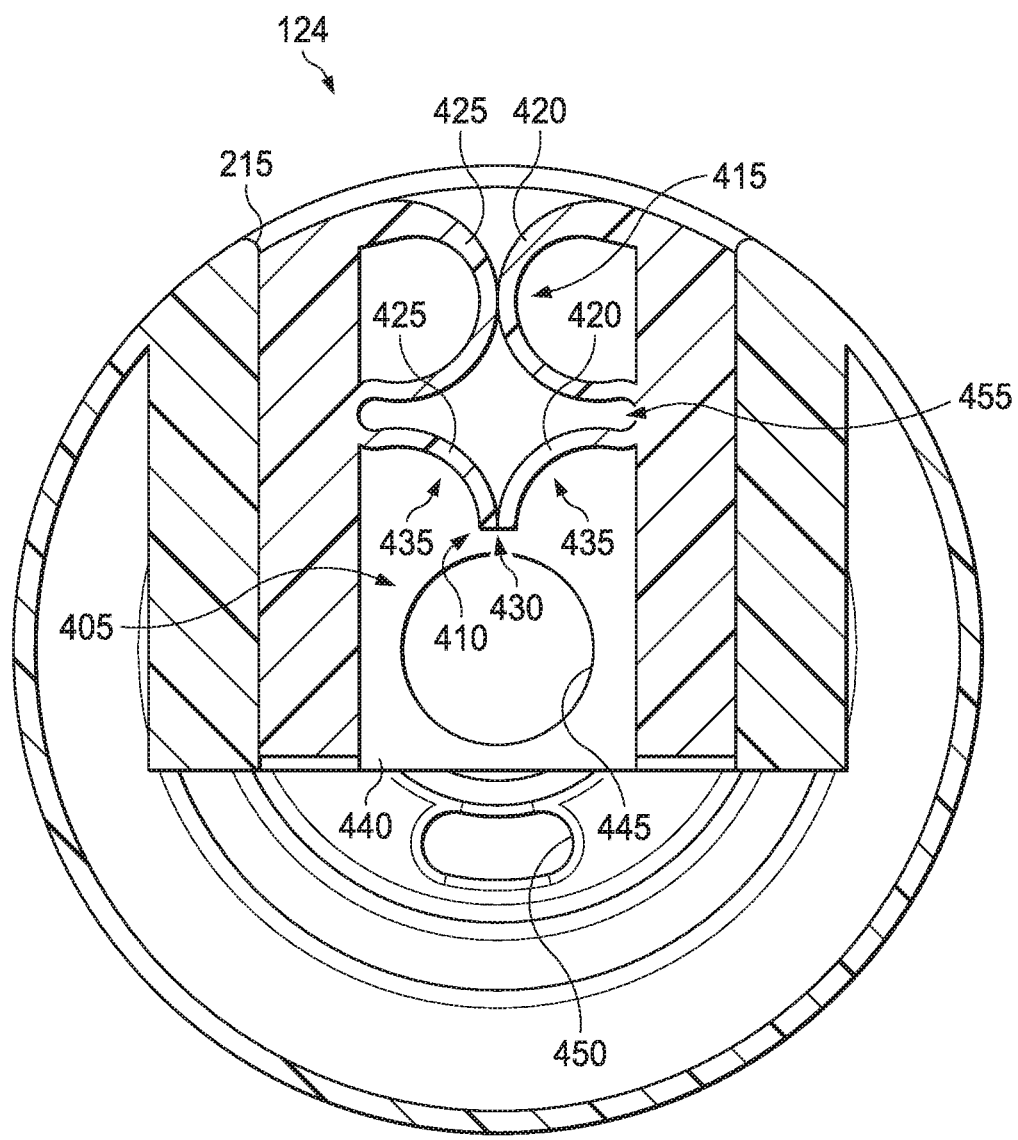
FIG. 4 is a section view of the sampling interface of FIG. 2.

FIG. 4 is a section view of the sampling interface 124 of FIG. 2 taken along line 4-4, illustrating additional details that may be associated with some example embodiments. As illustrated in the example of FIG. 4, the sampling interface 124 may comprise a sampling chamber 405. The sampling chamber 405 may be defined in part by the split seal 250 and a wall 440, which may have an aperture 445. In some embodiments, the sampling interface 124 may also comprise an ancillary fluid conductor, such as a conduit 450.

The split seal 250 may comprise more than one seal in some embodiments. For example, in the embodiment of FIG. 4, the split seal may 250 may comprise a first split seal 410 and a second split seal 415.

The first split seal 410 and the second split seal 415 may each comprise or consist essentially of two sealing members that converge to a sealing line. For example, the first split seal 410 may comprise a first sealing member 420 and a second sealing member 425 that converge to a sealing line 430. In the embodiment of FIG. 4, the first sealing member 420 abuts the second sealing member 425 to form the sealing line 430. As illustrated in FIG. 4, the first sealing member 420 and the second sealing member 425 may form external surfaces that can converge at less than a straight angle to form the sealing line 430. For example, the external surfaces of the first sealing member 420 and the second sealing member 425 may be convex as illustrated in FIG. 4. In some embodiments, the external surfaces may converge at a zero angle to form the sealing line 430.

The second split seal 415 may be disposed between the first split seal 410 and the sampling port 215 in some embodiments. The second split seal 415 may also comprise a first sealing member 420 and a second sealing member 425.

One or more fluid collection channels may also be disposed within the sampling interface 124 interior to the split seal 250. As illustrated in FIG. 4, interior collection channels 435 may be integral to the split seal 250 may be integral to the split seal 250. For example, the interior collection channels 435 may be formed at least in part by a concave interior surface of the first split seal 410, as illustrated in the example of FIG. 4. Additionally or alternatively, one or more intermediate collection channels 455 may be disposed between the first split seal 410 and the second split seal 415, and in some embodiments may be formed by exterior surfaces of the first split seal 410 and the second split seal 415.

Figure 5:
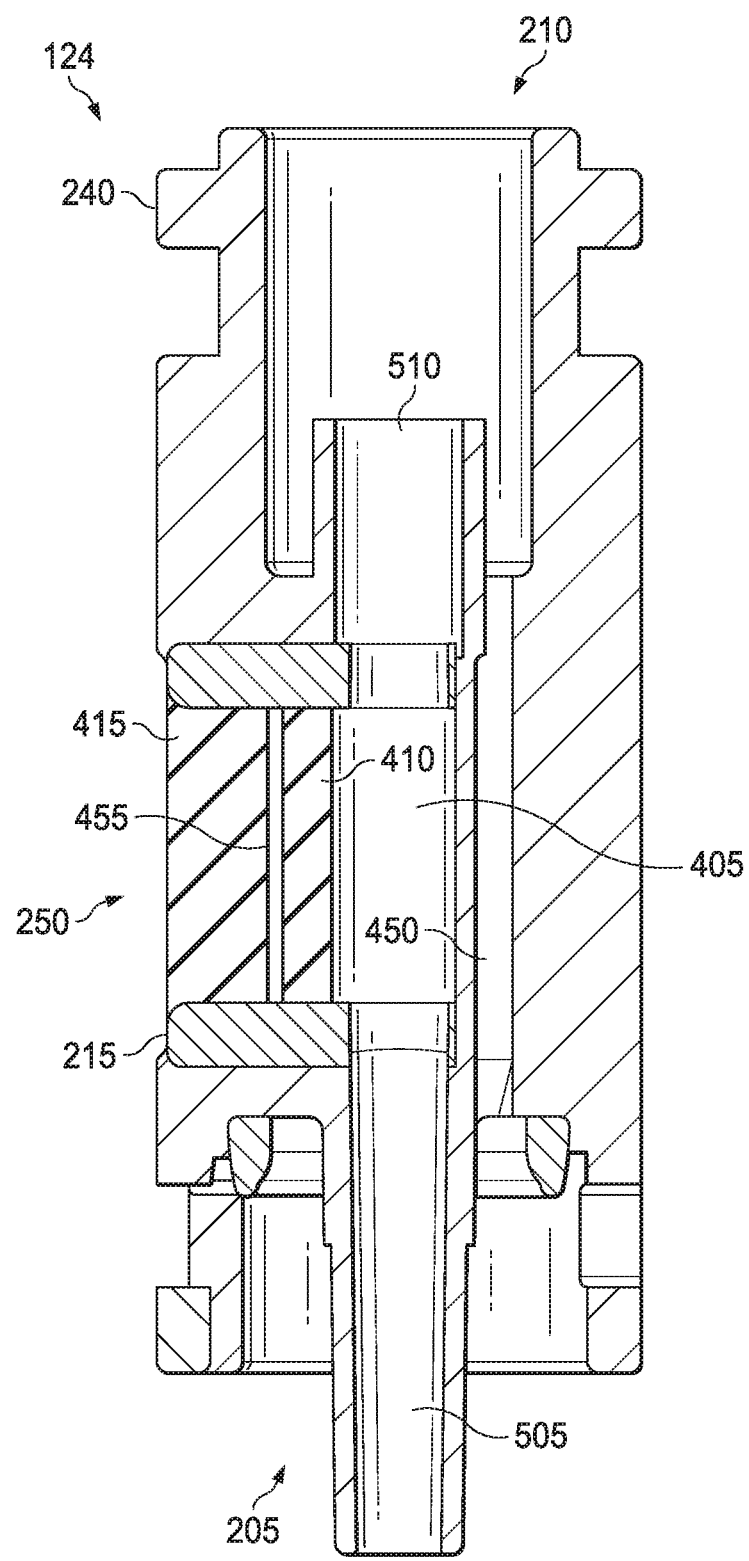
FIG. 5 is another section view of the sampling interface of FIG. 2.

FIG. 5 is a section view of the sampling interface 124 of FIG. 2 taken along line 5-5, illustrating additional details that may be associated with some example embodiments. As illustrated in the example of FIG. 5, the sampling interface 124 may comprise one or more fluid conductors, such as an inlet conduit 505 and an outlet conduit 510. In the example of FIG. 5, the inlet conduit 505 and the outlet conduit 510 are axially aligned along a length of the sampling interface 124, and the sampling chamber is disposed between the inlet conduit 505 and the outlet conduit 510. The inlet conduit 505 may pass through the fitting 220 and fluidly couple the sampling chamber 405 to the inlet port 205. Similarly, the outlet conduit 510 may fluidly couple the sampling chamber 405 to the outlet port 210.

The split seal 250 may be coupled to the sampling port 215 in some embodiments. For example, an interference fit may couple the insert 320 to the sampling port 215 in some embodiments. In other examples, a sealing member may be bonded directly to a side wall of the sampling port 215. As illustrated in the example of FIG. 5, the split seal 250 may be oriented within the sampling port 215 so that the intermediate collection channel 455 is substantially parallel to the fluid path through the sampling chamber 405. One or more of the interior collection channels 435 (not shown in FIG. 5) may also be oriented substantially parallel to the fluid path through the sampling chamber 405.

Figure 6A:
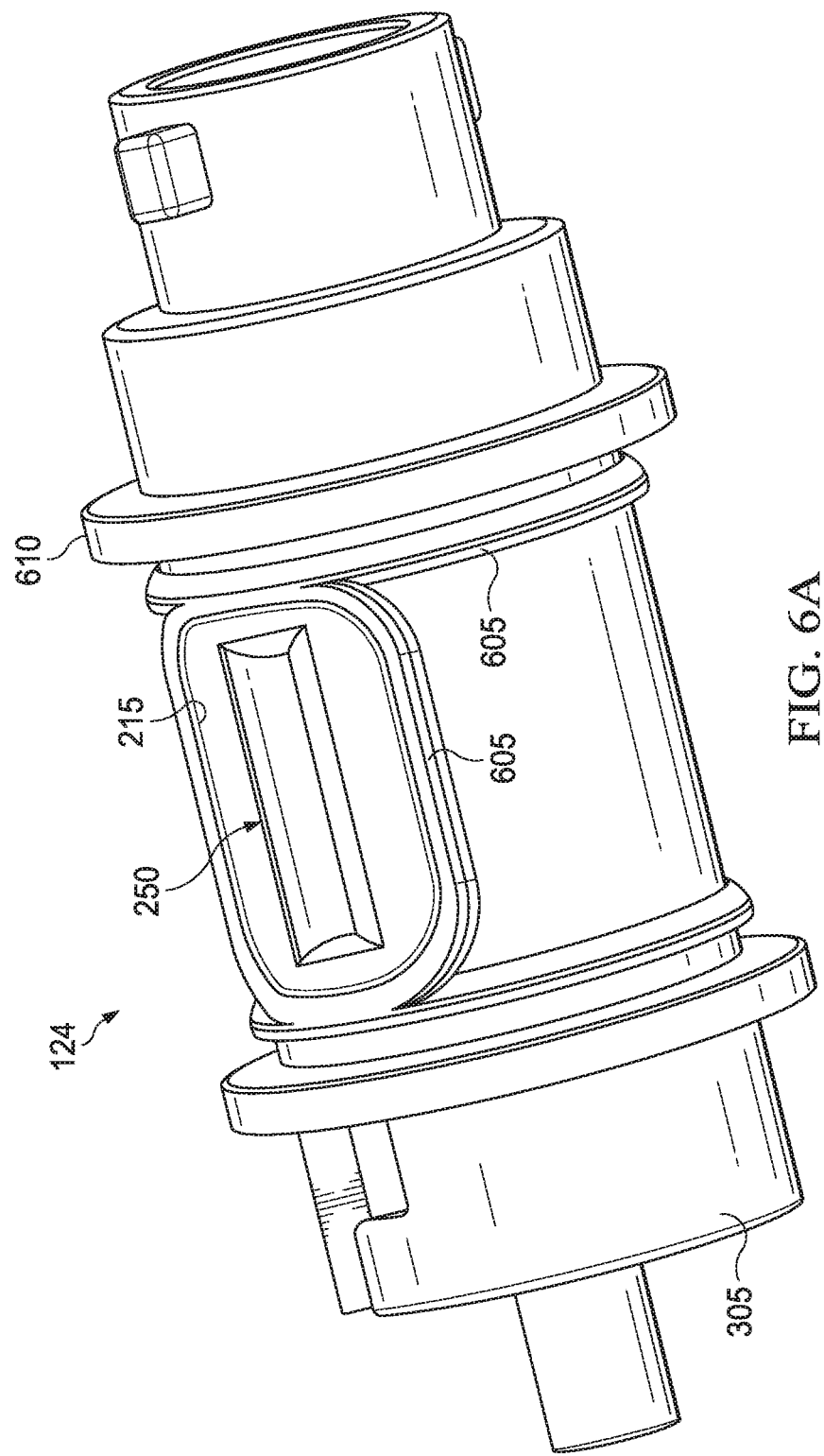
FIGS. 6A-6B are perspective views of another example embodiment of a sampling interface.
Figure 6B:
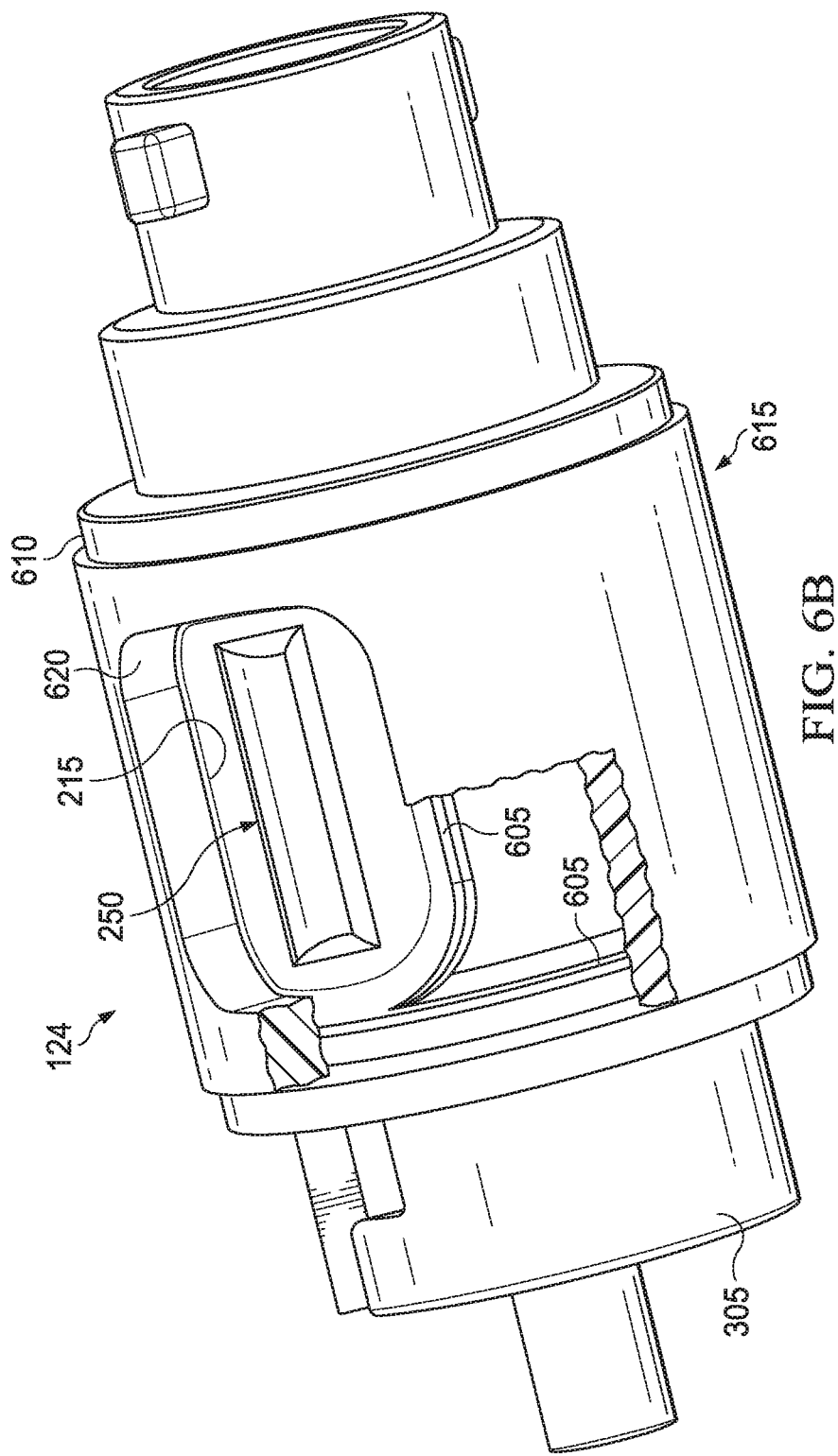

FIGS. 6A-6B are perspective views of another example embodiment of the sampling interface 124. The embodiment illustrated in FIGS. 6A-6B is similar in many respects to the example embodiment of FIGS. 2-5. As illustrated in FIG. 6A, some embodiments may additionally comprise one or more ribs 605. One or more guide collars 610 may be disposed around the housing 305 to facilitate rotation of a cover. For example, the ribs 605 can combine with a cover 615 to form seal around the sampling port 215 as illustrated in FIG. 6B. In some embodiments, a suitable cover may be a soft, dense polymer cover that can slip over the sampling interface 124 or clip onto the housing 305. A cover may have an aperture 620 similar to the sampling port 215 in size and shape, which can be aligned with the sampling port 215 to provide access to the split seal 250 for sampling, or may be offset or misaligned to facilitate maintaining a seal.

FIG. 7 is a schematic diagram of an example of a lateral flow strip 700 that may be associated with some embodiments of the sampling interface 124 for sampling fluid. In the example embodiment of FIG. 7, the lateral flow strip 700 may comprise an acquisition medium 705, a migration medium 710, and one or more test media, such as a test medium 715, a test medium 720, a test medium 725, a test medium 730, and a test medium 735.

The acquisition medium 705 is preferably adapted to wick or direct fluid toward the migration medium 710. In some examples, the acquisition medium 705 may comprise or consist essentially of a hydrophilic wicking material. In other examples, the acquisition medium 705 may comprise or consist essentially of a hydrophobic material with a hydrophilic treatment, such as adhesive patterning, or a combination of hydrophilic and hydrophobic material in some embodiments.

The migration medium 710 is preferably adapted to wick or direct fluid toward each of test media, and may have properties similar to the acquisition medium 705 in some embodiments. In some examples, the migration medium 710 may fluidly couple the acquisition medium 705 to one or more of the test media. In the example of FIG. 7, the migration medium 710 fluidly couples the acquisition medium 705 to each of the test media in series. In other example configurations, the migration medium 710 may be configured to distribute fluid to each of the test media in parallel.

A test medium is preferably configured to indicate a constituent of a fluid exposed to the test medium, such as a concentration of a specific enzyme, metabolite, or protein. A scale or chromatic indicator may be used to analyze the results, such as the type, count or concentration of a targeted constituent. For example, some embodiments of the lateral flow strip 700 may be configured to monitor wound progression, and one or more of the test media may be configured to indicate the concentration of certain matrix metalloproteinases (MMPs) such as MMP-1, MMP-2 MMP-8, MMP-9, or certain tissue inhibitors of metalloproteinases (TIMPs) such as TIMP-1 or TIMP-2. In other examples, one or more test media may be configured to detect infection, such as by indicating the concentration of certain pro-inflammatory and anti-inflammatory cytokines. For example, the test medium may be configured to indicate the concentration of interleukins (ILs) such as IL-1, IL-2, IL-6 or IL-10. Additionally or alternatively, one or more of the test media may be configured to measure pH, indicate the presence of gram positive or gram negative bacteria, or indicate the bacterial load count, for example.

Some embodiments of the lateral flow strip 700 may additionally comprise a progress indicator. For example, a progress indicator may be configured to indicate a sufficient exposure time, or indicate that a sufficient sample has been acquired. The example embodiment of FIG. 7 comprises a progress indicator 740 along an edge of the migration medium 710. The progress indicator 740 may be configured to be activated by or react with fluid in some embodiments, such as fluid transferred from the migration medium 710. In some embodiments, for example, the progress indicator 740 may be configured to change color in reaction to fluid exposure.

FIG. 8 is a schematic cross section of an example embodiment of the lateral flow strip 700. As illustrated in the example embodiment of FIG. 8, the lateral flow strip 700 may comprise a cover 805 that is substantially impermeable to liquid, and may be transparent or translucent. The cover 805 generally encloses the migration medium 710 and the test media. The acquisition medium 705 may extend or protrude from the cover 805 in some embodiments.

Figure 9:
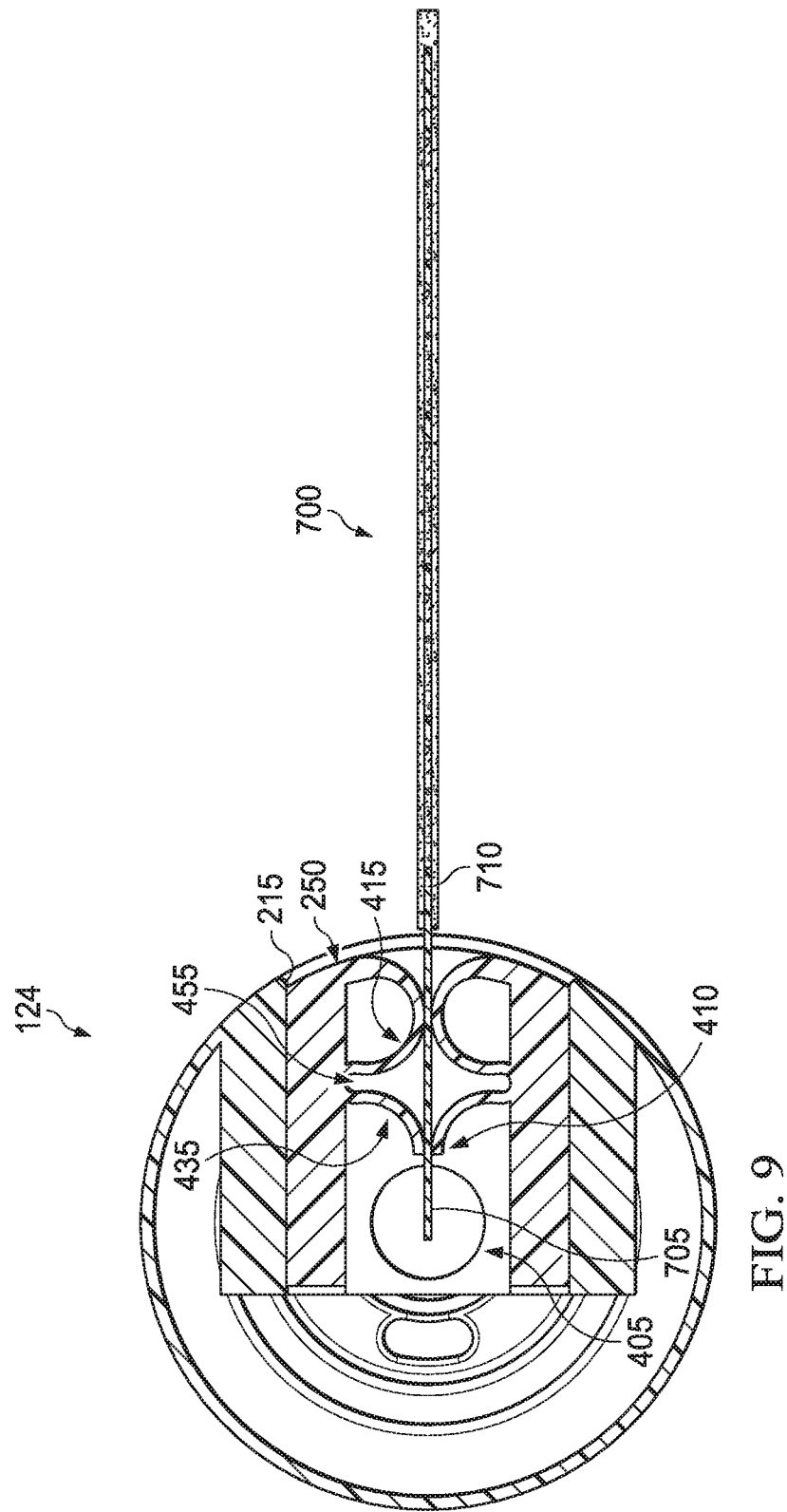
FIG. 9 is a schematic diagram illustrating an embodiment of the lateral flow strip of FIG. 7 with the sampling interface of FIG. 2.

In operation, the acquisition medium 705 may be inserted into a fluid for testing or sampling. For example, the schematic diagram of FIG. 9 illustrates an embodiment of the lateral flow strip 700 in which the acquisition medium 705 is generally sized and shaped for insertion into the sampling interface 124 to acquire a sample of exudate flowing through the sampling chamber 405. The split seal 250 is preferably sufficiently flexible to accommodate varying thickness of the acquisition medium 705, and sufficiently rigid to maintain sealing contact with the acquisition medium 705. The length of the acquisition medium 705 may vary, but preferably has sufficient length to extend past the split seal 250 into the sampling chamber 405. In some embodiments, the migration medium 710 may be wider than the acquisition medium 705, and may be wider than the sampling port 215 to prevent insertion of the migration medium 710 through the split seal 250. In embodiments having more than one split seal, a secondary split seal can be disposed between a primary split seal and the sampling port 215 to provide additional stability to the lateral flow strip 700. For example, as illustrated in the embodiment of FIG. 9, the second split seal 415 may be disposed between the first split seal 410 and the sampling port 215.

The split seal 250 is preferably sufficiently rigid to maintain sealing contact with the lateral flow strip 700 until the lateral flow strip 700 is removed from the sampling interface 124. The split seal 250 is also preferably configured to apply pressure to the lateral flow strip 700 if it is removed from the sampling interface 124, wiping any excess fluid from the surface of the lateral flow strip 700. For example, if the lateral flow strip 700 of FIG. 9 is removed, the first split seal 410 may remove fluid from the acquisition medium 705 and direct the fluid into an internal fluid collection channel, such as the interior collection channel 435 disposed between the sampling chamber 405 and the first split seal 410. The second split seal 415 may remove additional fluid and direct it into an intermediate collection channel, such as the intermediate collection channel 455 disposed between the first split seal 410 and the second split seal 415.

Figure 10A:
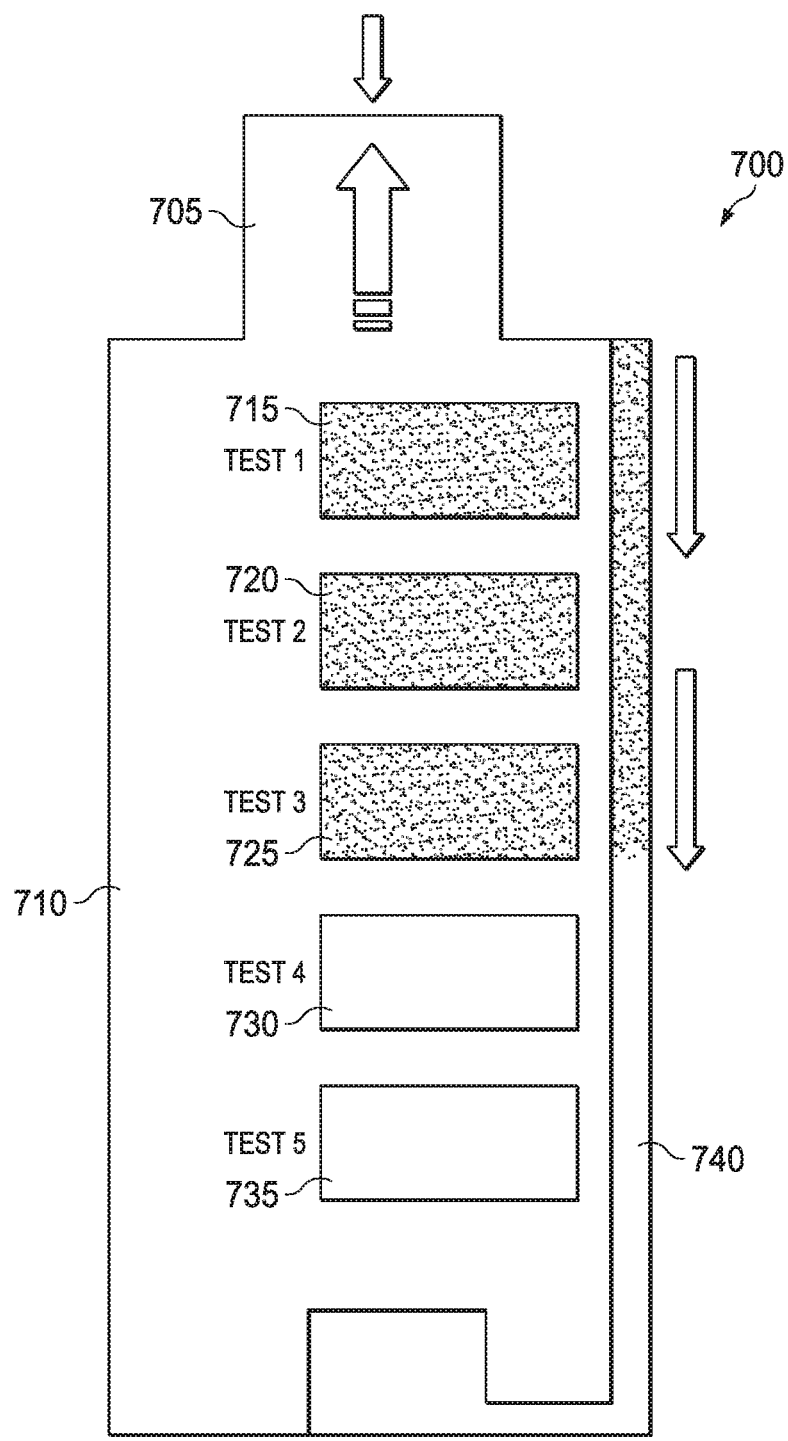
FIG. 10A is a schematic diagram of the lateral flow strip of FIG. 7, illustrating a partially completed sample.
Figure 10B:
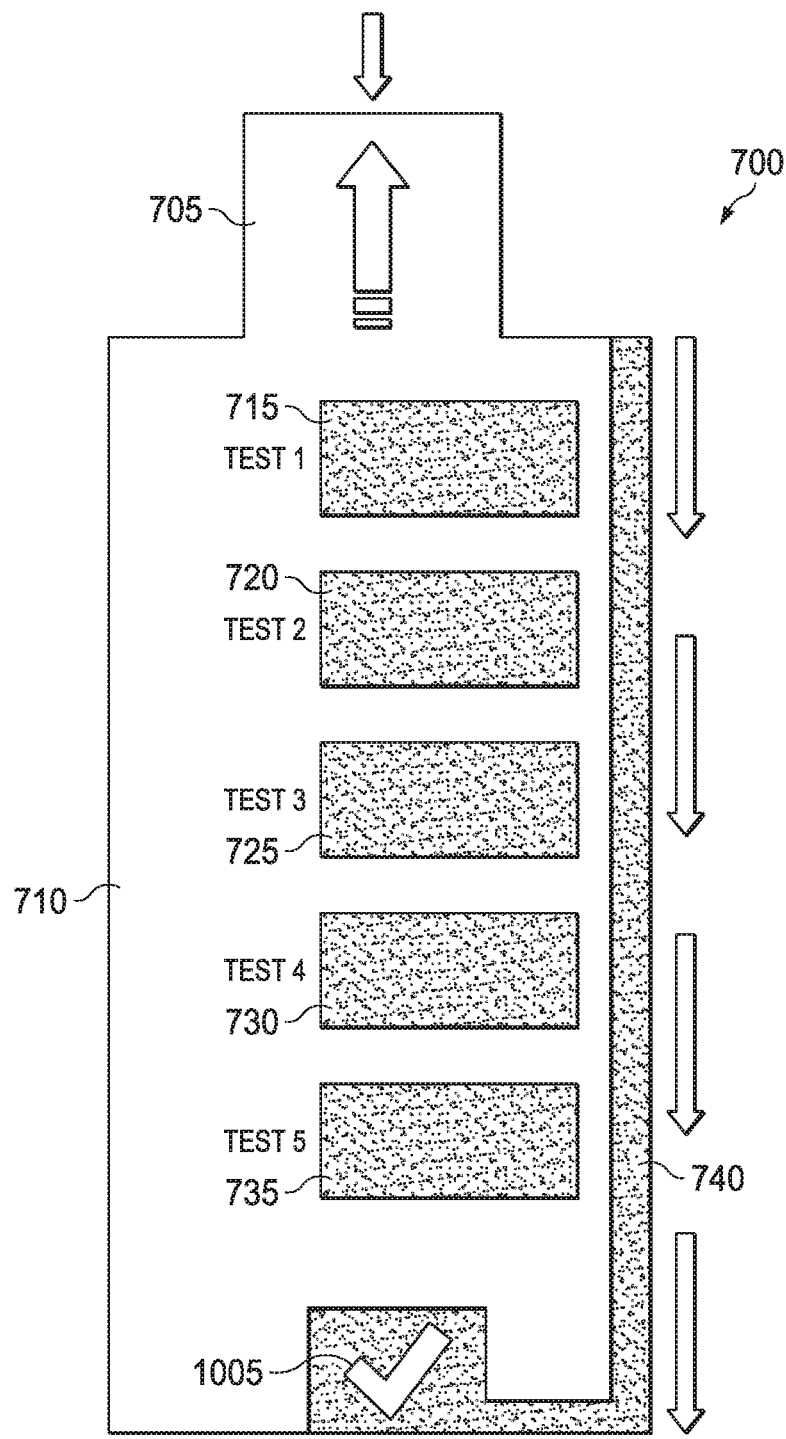
FIG. 10B is a schematic diagram of the lateral flow strip of FIG. 7 illustrating a completed sample.

The acquisition medium 705 may wick or otherwise distribute acquired fluid to the migration medium 710, which can wick or otherwise distribute acquired fluid through the test media. FIG. 10A is a schematic diagram of the lateral flow strip 700 of FIG. 7, illustrating a partially completed sample. FIG. 10B is a schematic diagram of the lateral flow strip 700 of FIG. 7, illustrated a completed sample. In the example of FIG. 10A and FIG. 10B, the migration medium 710 is configured to move fluid through the test media, and concurrently along the progress indicator 740. In the example of FIG. 10A, fluid is partially distributed through the test media and the progress indicator 740, so that the progress indicator 740 indicates that only test medium 715, test medium 720, and test medium 725 have been exposed to fluid. FIG. 10B is a schematic diagram of the lateral flow strip 700 of FIG. 7 illustrating that all test media have been exposed to fluid. FIG. 10B further illustrates an example embodiment of the lateral flow strip 700 having a tick mark 1005 or other symbol indicative of a completed sample.

In other examples, a sampling interface similar or analogous to the sampling interface 124 may be integrated with or coupled to a dressing interface. For example, a sampling interface may be disposed proximate to a tube connection, preferably furthest away from a dressing to minimize cross-contamination from the dressing. In yet other examples, a sampling interface similar or analogous to the sampling interface 124 may be integrated with or coupled to a container, such as the container 112. For example, in some embodiments, a sampling interface may be coupled to an inlet of a container to allow fluid to be sampled as it enters.

The systems, apparatuses, and methods described herein may provide significant advantages. For example, wound biomarkers can be sampled to provide diagnostic insight without discontinuing or interrupting therapy, removing a dressing, or disrupting a patient. The sampling interface 124 can facilitate serial diagnostics for proactively detecting infections or stalled wounds before they develop visual clues, odors, or develop into a more serious condition. Additionally, some wound locations may be difficult to access, such as sacral wounds. The sampling interface 124 can provide more convenient access to fluid, and can moved if advantageous.

While shown in a few illustrative embodiments, a person having ordinary skill in the art will recognize that the systems, apparatuses, and methods described herein are susceptible to various changes and modifications. Features or elements described in the context of one example may be combined or replaced with feature or elements described in other examples. Moreover, descriptions of various alternatives using terms such as "or" do not require mutual exclusivity unless clearly required by the context, and the indefinite articles "a" or "an" do not limit the subject to a single instance unless clearly required by the context. Components may be also be combined or eliminated in various configurations for purposes of sale, manufacture, assembly, or use. For example, in some configurations the sampling interface 124, the lateral flow strip 700, or both may be separated from other components for manufacture or sale.

The appended claims set forth novel and inventive aspects of the subject matter described above, but the claims may also encompass additional subject matter not specifically recited in detail. For example, certain features, elements, or aspects may be omitted from the claims if not necessary to distinguish the novel and inventive features from what is already known to a person having ordinary skill in the art. Features, elements, and aspects described herein may also be combined or replaced by alternative features serving the same, equivalent, or similar purpose without departing from the scope of the invention defined by the appended claims.

What is claimed is:

1. An apparatus for sampling fluid removed from a tissue site, the apparatus comprising:
    an inlet port;
    an outlet port;
    a sampling chamber fluidly coupled to the inlet port and to the outlet port;
    a sampling port; and
    two separate split seals comprising:
        a first split seal disposed between the sampling port and the sampling chamber; and a second split seal disposed between the first split seal and the sampling port.

2. The apparatus of claim 1, wherein:
    the first split seal comprises a first sealing member and a second sealing member; and
    the first sealing member and the second sealing member converge to a sealing line.

3. The apparatus of claim 1, wherein:
    the first split seal comprises a first sealing member and a second sealing member; and
    the first sealing member abuts the second sealing member to form a sealing line.

4. The apparatus of claim 1, wherein:
    the first split seal comprises a first external surface and a second external surface;
    the first external surface and the second external surface are convex; and
    the first external surface and the second external surface converge to a sealing line.

5. The apparatus of claim 1, wherein:
    the first split seal comprises a first external surface and a second external surface; and
    the first external surface and the second external surface converge at less than a straight angle to form a sealing line.

6. The apparatus of claim 1, wherein:
    the first split seal comprises a first external surface and a second external surface;
    the first external surface and the second external surface are convex; and
    the first external surface and the second external surface converge at less than a straight angle to form a sealing line.

7. The apparatus of claim 1, wherein:
    the first split seal comprises a first external surface and a second external surface; and the first external surface and the second external surface converge at a zero angle to form a sealing line.

8. The apparatus of claim 1, further comprising a fluid collection channel disposed interior to the first split seal.

9. The apparatus of claim 8, wherein the fluid collection channel is formed by a concave interior surface of the first split seal.

10. The apparatus of claim 9, further comprising a second fluid collection channel disposed between the first split seal and the second split seal.

* * * * *